United States Patent [19]

Ashton et al.

[11] 3,932,403

[45] Jan. 13, 1976

[54] PHOSPHORUS ACID AMIDES

[75] Inventors: Stanley Ashton; Vijay Ratna Sharma; John Anthony Taylor, all of Manchester, England

[73] Assignee: Imperial Chemical Industries Limited, London, England

[22] Filed: July 20, 1973

[21] Appl. No.: 381,223

[30] Foreign Application Priority Data

July 24, 1972 United Kingdom............... 34478/72

[52] U.S. Cl....... 260/248 R; 260/256.5 R; 260/306; 260/307 D; 260/465.5 R; 260/470; 260/551 P; 260/551 S; 260/556 AR; 260/561 S; 260/562 R; 260/936; 260/937; 260/780; 260/940; 260/941; 260/947
[51] Int. Cl.$^2$..... C07F 9/22; C07F 9/24; C07F 9/26
[58] Field of Search ........... 260/551, 556, 944, 936, 260/557, 561, 936, 941, 947, 543, 256.5, 306, 307, 465.5, 470, 562, 437, 248

[56] References Cited

UNITED STATES PATENTS

| | | | |
|---|---|---|---|
| 3,647,856 | 3/1972 | Josey et al............................ | 260/551 |
| 3,737,438 | 6/1973 | Roos et al............................ | 260/551 |
| 3,755,507 | 8/1973 | Brown et al. ....................... | 260/947 |

*Primary Examiner*—Harry I. Moatz
*Attorney, Agent, or Firm*—Cushman, Darby & Cushman

[57] ABSTRACT

Amides of phosphorus-containing acids are reacted with sulphenyl halides to give phosphorus-containing acid amides in which one or more of the nitrogen atoms carries the appropriate substitutent attached through a sulphur atom. These substituted amides are inhibitors of premature vulcanisation in rubbers. The most effective compounds are arylamides substituted by secondary alkylthio groups.

4 Claims, No Drawings

PHOSPHORUS ACID AMIDES

This invention relates to amides of phosphorus-containing acids of value as inhibitors of premature vulcanisation in rubbers.

It is customary in the manufacture of vulcanised rubbers to incorporate into the unvulcanised rubber various additives such as antioxidants, antiozonants, fillers, vulcanisation activators, etc., and lastly vulcanisation accelerators and a vulcanising agent such as sulphur. The compounded rubber is then shaped and finally raised to vulcanisation temperature. Before the final stage, however, some premature vulcanisation may take place, especially during the compounding stage in a mill or Banbury mixer when heat is generated, or during handling such as calendering or extruding, or in some cases even during storage. Premature vulcanisation causes the rubber to become lumpy with the result that subsequent processing or vulcanising operations cannot be carried out satisfactorily. Premature vulcanisation may be reduced by using delayed action accelerators of for example the benzthiazylsulphenamide type and also by the use of retarders such as N-nitrosodiphenylamine or salicylic acid, but these retarders frequently introduce other difficulties. No satisfactory means of preventing premature vulcanisation has hitherto been found and the increasing use of furnace carbon blacks and of antioxidants and antiozonants based on p-phenylenediamine has exacerbated the problem. It has now been found that certain novel N-substituted amides of phosphorus-containing acids are powerful inhibitors of premature vulcanisation.

According to the invention there are provided amides of the formula

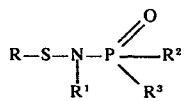

(I)

wherein R is an optionally-substituted hydrocarbyl group, $R^1$ is a hydrogen atom, an optionally-substituted hydrocarbyl group, or a group -$SO_2$-R, -CO-R, -S-R, or -N=CHR and $R^2$ and $R^3$, which may be the same or different, are each a group R-S-$NR^1$- or a hydrogen or halogen atom or an optionally-substituted alkyl, alkenyl, cycloalkyl, aryl, alkoxy, alkenoxy, cycloalkyloxy, aryloxy, alkylthio, alkenylthio, cycloalkylthio, arylthio or heterocyclylthio group or an amino or substituted amino group or $R^2$ and $R^3$ together with the phosphorus atom form a heterocyclic ring or $R^1$ and $R^2$ together with the phosphorus and nitrogen atoms form a heterocyclic ring.

As examples of groups which may be represented by R or $R^1$ there are mentioned alkyl groups such as methyl, ethyl, propyl, isopropyl, butyl, isobutyl, tert.-butyl, hexyl, n-octyl, tert.-octyl, n-dodecyl, tert.-dodecyl and n-octadecyl, alkenyl groups such as propenyl, n-but-1-enyl, isobutenyl, n-pent-1-enyl, dodecenyl and n-octadecenyl, cycloalkyl groups such as cyclopentyl and cyclohexyl, aryl groups such as phenyl, o-, m- and p-tolyl and naphthyl, and substituted hydrocarbyl groups such as β-methoxyethyl, alkyloxycarbonylethyl, β-cyanoethyl, 2-formylprop-2-yl, 4-chlorophenyl, 4-methoxyphenyl, 4-dimethylaminophenyl, 2-nitrophenyl, 4-nitrophenyl, 2,3,4,5,6-pentachlorophenyl, 2-methoxycarbonylphenyl and 4-phenylsulphonylphenyl.

R may also be a divalent or polyvalent hydroxycarbyl group linking through sulphur atoms two or more amides of phosphorus-containing acid groups, for example alkylene, p-phenylene, cyclooctylene or cyclododecylene.

$R^1$ may also be an alkyl or arylsulphonyl group such as p-toluenesulphonyl, an optionally substituted alkylideneamino group such as benzylideneamino, an alkyl or arylcarbonyl group such as acetyl or an alkyl or arylthio group or optionally substituted derivative of any one of these.

In those amides which contain two or more groups R or $R^1$ the groups R or the groups $R^1$ may be the same or different.

It is preferred that R be an alkyl group, especially a secondary alkyl, or a cycloalkyl group.

It is preferred that $R^1$ by an optionally substituted aryl group, especially phenyl.

As a halogen atom which may be represented by $R^2$ or $R^3$ there is mentioned bromine and, especially, chlorine.

As examples of groups which may be represented by $R^2$ or $R^3$ there are mentioned the alkyl, alkenyl, cycloalkyl and aryl groups and substituted derivatives thereof which may be represented by R or $R^1$ and alkoxy, alkenyloxy, cycloalkyloxy, aryloxy, alkylthio, alkenylthio, cycloalkylthio and arylthio groups and substituted derivatives thereof derived from such groups.

As examples of heterocyclylthio groups which may be represented by $R^2$ or $R^3$ there are mentioned 2-benzothiazolylthio, 2-benzoxazolythio, 2-benzimidazolylthio, 2-pyrimidinylthio and 2-triazinylthio groups.

As examples of substituted amino groups which may be represented by $R^2$ or $R^3$ there are mentioned ethylamino, diethylamino, dimethylamino, phenylamino, methylphenylamino and ethylphenylamino.

As examples of heterocyclic rings which may be formed from $R^2$ and $R^3$ together with the phosphorus atom there are mentioned 2-oxo-1,3,2-diazaphospholane, 2-oxo-4,5-benzo-1,3,2-diazaphospholane, 2-oxo-1,3,2-oxozaphosphloane, 2-oxo-4,5-benzo-1,3,2-oxazaphospholane, 2-oxo-4,5-benzo-1,3,2-oxazaphospholane, 2-oxo-4,5-benzo-1,3-thiazaphospholane, and 2-oxo-2,3,-dithiaphospholane.

As examples of amides of this invention there are mentioned N,$N^1$,$N^{11}$-tris-(isopropylthio)-N,$N^1$,$N^{11}$-triphenylphosphoric triamide, N,$N^1$,$N^{11}$-tris-(n-butylthio)-N,$N^1$,$N^{11}$-triphenylphosphoric triamide, N,$N^1$,$N^{11}$-tris-(cyclohexylthio)-N,$N^1$,$N^{11}$-triphenylphosphoric triamide, N,$N^1$,$N^{11}$-tris-(benzylthio)-N,$N^1$$N^{11}$-tris(p-methoxyphenyl)phosphoric triamide, N,$N^1$,$N^{11}$-tris-(n-dodecylthio)-N,$N^1$,$N^{11}$-tris (o-chlorophenyl)-phosphoric triamide, N,$N^1$,$N^{11}$-tris-(tert.-octylthio)-N,$N^1$,$N^{11}$-triphenylphosphoric triamide, N,$N^1$,$N^{11}$-tris-(n-octadecylthio)-N,$N^1$,$N^{11}$-tris-(p-dimethylaminophenyl) phosphoric triamide, N,$N^1$,$N^{11}$-tris-(methylthio)-N,$N^1$,$N^{11}$-trimethylphosphoric triamide, N,$N^1$,$N^{11}$-tris-(isopropylthio)-N,$N^1$,$N^{11}$-trimethylphosphoric triamide, N,$N^1$,$N^{11}$-tris-(isopropylthio)-N,$N^1$,$N^{11}$-cyclohexylphosphoric triamide, N,$N^1$,$N^{11}$-tris-(cyclohexylthio)-N,$N^1$,$N^{11}$-trimethylphosphoric triamide, N,$N^1$-bis-(butylthio)-N,$N^1$-diphenyl-$N^{11}$-diethylenoxyphosphoric triamide, N,$N^1$,$N^{11}$-tris-(phenylthio)-N,$N^1$,$N^{11}$-triphenylphosphoric triamide, N,$N^1$,$N^{11}$-tris-(p-methoxyphenylthio)-N,$N^1$,$N^{11}$-triphenylphosphoric triamide, N,$N^1$,$N^{11}$-tris(isopropylthio)-2-anilino-2-oxo-1,3,2-diazaphospholane, N,$N^1$,$N^{11}$-tris-(cyclohexylthio)-2-methylamino-4,5-benzo-1,3,2-diazaphospholane, methyl-N,N¹-bis-(sec-butylthio)-N,N¹-diphenylphosphorodiamidate, phenyl-N,N¹-bis-(methylthio)-N,N¹-diphenylphosphorodiamidate, ethyl-N,N¹-bis-(n-dodecylthio)-N,N¹-bis-(o-tolyl)phosphorodiamidate, ethyl-N,N¹-bis-(cyclohexylthio)-N,N¹-diethylphosphorodiamidate, phenyl-N,N¹-bis-(tert.-octylthio)-N,N¹-dimethyl phosphorodiamidate, diethyl-N-phenyl-N-(iso-propylthio)-phospho-amidate, 2-methoxy-2-oxo-1,3,2-diazaphospholane, 2-phenoxy-2-oxo-1,3-bis-(sec-butylthio)-4,5-benzo-1,3,2-diazaphospholane, N-isopropylthiophenylphosphoramidic acid dichloride, N,N¹-bis-(n-butylthio)-N,N¹-diphenyl phosphorodiamidic acid chloride, N,N¹-bis-(phenylthio)-N,N¹-dimethylphosphorodiamidic acid chloride, N,N¹-bis-(p-tolylthio)-N,N¹-diphenyl-phosphoric diamide, N,N¹-bis-(methylthio)-N,N¹-dimethyl-phosphoric diamide, N,N¹-bis-(p-chlorophenylthio)-N,N¹-di-(cyclohexyl)-phosphoric diamide, 1,3-bis-(isopropylthio)-2-phenyl-2-oxo-1,3,2-diazaphosphospholane, N-phenyl-N-(cyclohexylthio)-dimethylphosphinic amide, N-(p-nitrophenyl)-N-(sec-butylthio)-diethylphosphinic amide, N-methyl-N-(tert.-butylthio)-diphenylphosphinic amide, N-(benzylthio)-N-cyclohexyldiphenylphosphinic amide and 1,3-di(isopropyl=thio)-2-ethoxy-2-oxo-4,5-benzo-1,3,2-diazaphospholane.

According to the invention there is also provided a process for the manufacture of amides of the formula I which comprises reacting a compound of the formula

(II)

with a sulphenyl halide of the formula R - S - Halogen wherein R¹ has the meaning given hereinbefore and R⁴ and R⁵ are each a group of the type represented by R² and R³.

The process is conveniently carried out at a temperature below 100°C and preferably between −10° and 50°, preferably in an inert solvent such as cyclohexane, carbon tetrachloride, dimethylformamide or toluene, and in presence of an acid binding agent such as pyridine, triethylamine, N,N-dimethylaniline or potassium carbonate. Mixtures of inert solvents may be used and improved yields are sometimes obtained when one component, which may be present in comparative small proportions, is of a polar nature, e.g. dimethyl formamide.

The amount of sulphenyl halide, peferably sulphenyl chloride or bromide, is preferably about 1 molar proportion for each -NHR¹ group. In these circumstances a group R⁴ or R⁵ which represents a -NHR¹ group will be converted into a group -NR¹-SR. If a deficiency of sulphenyl halide is used only a corresponding proportion of the groups of the type -NHR¹ will be converted into groups -NR¹-SR. In those cases in which R¹ is a hydrogen atom the use of excess sulphenyl halide may lead to amides in which R¹ is a group -RS.

The amide of formula I may be conveniently isolated by removal of most of the solvent under reduced pressure and crystallisation in the case of solids. Suitable solvents for crystallisation include alcohol, hexane, chloroform and toluene. Where the products are liquids purification is most readily effected by chromatography over silica gel or alumina.

As compounds of formula II which may be used in the process of the invention there may be mentioned phosphoric triamides, e.g. N,N¹,N¹¹-triphenyl phosphoric triamide, N,N¹,N¹¹-tri-(p-methoxyphenyl) phosphoric triamide, N,N¹,N¹¹-tri-(p-tolyl) phosphoric triamide, N,N¹,N¹¹-tri-(o-tolyl) phosphoric triamide, N,N¹,N¹¹-tri-(p-chlorophenyl) phosphoric triamide, N,N¹,N¹¹-tri-(phenylsulphonylphenyl) phosphoric triamide, N,N¹,N¹¹-tri-(p-dimethylaminophenyl) phosphoric triamide, N,N¹,N¹¹-tri-(p-nitrophenyl) phosphoric triamide, N,N¹,N¹¹-trimethyl-phosphoric triamide, N,N¹N¹¹-triethylphosphoric triamide, N,N¹,N¹¹-tris-cyclohexylphosphoric triamide, N,N¹,N¹¹-tris-(tert.-octyl) phosphoric triamide, N,N¹,N¹¹-tri-(n-octyl) phosphoric triamide, N,N¹,N¹¹-tri-(n-dodecyl) phosphoric triamide, N,N¹,N¹¹-tris-(tert.-hexadecyl) phosphoric triamide, N,N¹,N¹¹-tri-(n-octadecyl) phosphoric triamide, N¹-phenyl-N¹,N¹¹-bis-(morpholyl) phosphoric triamide, 2-anilino-2-oxo-1,3,2-diazaphospholane and 2-methylamino-2-oxo-1,3,2-diazaphospholane, phosphorodiamidates such as methyl-N,N¹-diphenylphosphorodiamidate, phenyl-N,N¹-diphenylphosphorodiamidate, cyclohexyl-N,N¹-diphenylphosphorodiamidate, ethyl-N,N-dimethyl-N¹-phenyl-phosphorodiamidate, ethyl-N,N¹-di-(o-tolyl) phosphorodiamidate, ethyl-N,N¹-di-(p-methoxyphenyl) phosphorodiamidate, ethyl-N,N¹-diethyl phosphoramidate, phenyl-N,N¹-di-(isopropyl) phosphorodiamidate, methyl-N,N¹-di-(cyclohexyl) phosphorodiamidate and ethyl-N,N-diethyleneoxy-N¹-phenyl phosphorodiamidate, -N-alkyl phosphoroamidates such as diethyl-N-phenyl phosphoramidate diethyl-N-(o-tolyl) phosphoramidate, diethyl-N-methyl phosphoamidate, diphenyl-N-cyclohexyl phosphoramidate, dimethyl-N-(n-dodecyl) phosphoramidate, 2-methoxy-2-oxo-1,3,2-diazophospholane and 2-phenoxy-2-oxo-4,5-benzo-1,3,2-diazaphospholane, acid chlorides of substituted phosphoramidic acids such as phenylphosphoramidic acid dichloride and cyclohexylphosphoramidic acid dichloride, chlorides of substituted phosphorodiamidic acids such as N,N¹-diphenyl phosphorodiamidic acid chloride, N,N-diethyleneoxy-N¹-phenyl phosphorodiamidic acid chloride, N,N¹-dimethyl phosphorodiamidic acid chloride, phosphonic diamides such as N,N¹-diphenylphosphonic diamide, N,N¹-di(p-tolyl) phosphonic diamide, N,N¹-dimethyl phosphonic diamide, N,N¹-diethyl phosphonic diamide, N,N¹-di-(cyclohexyl) phosphonic diamide, N,N¹-di-(p-methoxyphenyl) phosphonic diamide, N-phenyl-N¹-methylphosphonic diamide, N,N¹-di-(p-chlorophenyl) phosphonic diamide and 2-phenyl-2-oxo-1,3,2-diazaphospholane and phosphinic amides such as N-phenyl-dimethyl phosphinic amide, N-phenyldiphenylphosphinic amide, N-(p-nitrophenyl dimethylphosphinic amide, N-(o-chlorophenyl)-diethylphosphinic amide, N-methyl diphenylphosphinic amide and N-(cyclohexyl diphenyl phosphinic amide.

According to the invention there is further provided a process for reducing the premature vulcanisation of a rubber containing a vulcanising agent and a vulcanisation accelerator which comprises incorporating in the rubber an amide of the formula I.

The vulcanising agent used in this second process of the invention may be a sulphur donor, such as N,N'-dithiobismorpholine, N,N'-dithiobis-caprolactam, tetramethylthiuram disulphide, diethylthiophenyl disulphide or diethylthiophenyl trisulphide or preferably elemental sulphur, or for example a peroxide or other type of vulcanising agent.

The vulcanisation accelerator used in the second process of the invention is preferably a sulphenamide such as N-cyclohexylbenzothiazole-2-sulphenamide, N-t-butylbenzothiazole-2-sulphenamide, N-diethyleneoxybenzothiazole-2-sulphenamide or N-dicyclohexylbenzothiazole-2-sulphenamide, a thiazole such as mercaptothiazole, 2-mercaptobenzothiazole or its metal salts e.g. zinc, sodium or copper salt or dibenzothiazyl disulphide or a thiuram such as tetramethylthiuram monosulphide, tetramethylthiuram disulphide, tetramethylthiuram tetrasulphide, tetraethylthiuram monosulphide, tetraethylthiuram disulphide, or a metal salt of a dithiocarbamate such as zinc dimethyldithiocarbamate or sodium diethyldithiocarbamate.

Other types of accelerator may however be used such as diaryl guanidines, thioureas, xanthates or aldehyde-amine condensates, or mixtures of any of these and the above accelerators.

Amides of the formula I in which R is a trichloromethyl group are effective as inhibitors of premature vulcanisation using a thiazole accelerator such as 2-mercaptobenzthiazole, but much less effective with sulphenamide accelerators.

The amounts of vulcanisation agent and accelerator may be those conventionally used in the manufacture of rubber vulcanisates.

The amount of amide may be from 0.01 percent to 5 percent and preferably from 0.05 to 2.5 percent of the weight of the rubber.

Rubbers which may be used in the second process of the invention include both natural and synthetic rubbers and mixtures thereof. The synthetic rubber may in general be any polymeric material containing olefinic unsaturation and capable of being cross-linked by particularly sulphur, but also be peroxide or other cross-linking agents. Examples of synthetic rubbers include cis-polybutadiene, butyl rubber, ethylene-propylene terpolymer, polymers of 1,3-butadienes such as isoprene and chloroprene and copolymers of 1,3-butadiene with other monomers such as styrene, acrylonitrile and isobutylene.

The amide may be incorporated into the rubber by any conventional dry rubber or latex compounding procedure, for example on a rubber mill, in an internal mixer, through a screw type extruder blender, as a solution in an organic solvent or as an aqueous dispersion. If desired the latex into which the amide has been incorporated may be coagulated and converted into dry raw rubber by conventional techniques and used subsequently for making vulcanisable compositions.

According to the invention there are also provided unvulcanised rubber compositions containing an amide of formula I.

The rubber mix may also contain conventional rubber adjuvants such as anitoxidants, antiozonants, fillers, peptising agents, pigments, blowing agents, and accelerator activators such as zinc oxide and stearic acid, or such adjuvants may be incorporated subsequently into the unvulcanised rubber composition.

The invention is of particular value when the rubber composition is reinforced with a furnace black or contains a p-phenylene diamine-based antiozonant since such rubber compositions are especially prone to premature vulcanisation.

Incorporation of the amide into the rubber may be assisted if the amide is blended with an inert inorganic diluent such as silica alumina, calcium carbonate or Fuller's earth. Such blends, which will preferably contain from 10 to 70 percent of the amide, represent another feature of the invention.

By the second process of the invention there are obtained vulcanisable rubber compositions which can be handled on conventional rubber processing machines or stored for long periods with little tendency to premature vulcanisation but which will cure readily at conventional vulcanisation temperatures to give vulcanisates of excellent physical properties. These vulcanisable rubber compositions, their vulcanisation by heating to conventional vulcanisation temperatures, and the vulcanisates so obtained are further features of this invention.

The invention is illustrated but not limited by the following Examples in which all parts and percentages are by weight unless otherwise stated.

EXAMPLE 1

A solution of 16.55 parts of isopropyl sulphenyl chloride in 150 parts of carbon tetrachloride was added slowly to a stirred mixture of 16.77 parts of $N,N^1,N^{11}$-triphenyl phosphoric trianilide and 18 parts of triethylamine in 150 parts of carbon tetrachloride. The mixture was filtered at 35°, and the solvent was removed from the filtrate under reduced pressure, to leave a viscous yellow oil which on trituration with petroleum ether (6.p. 60°–80°C) gave 14.6 parts of $N,N^1,N^{11}$-tris(isopropylthio) phosphoric acid trianilide, a colourless solid m.p. 115°–117°. The NMR spectrum was in accordance with the designated structure.

| Example 2 | Parts |
| --- | --- |
| Natural Rubber Smoked Sheets | 100 |
| Zinc Oxide | 3.5 |
| Stearic Acid | 3 |
| High Abrasion Furnace Black | 45 |
| Process Oil | 3.5 |
| Sulphur | 2.5 |
| N-Cyclohexyl-2-benzthiazylsulphenamide | 0.5 |
| $N,N^1,N^{11}$-tris-(isopropylthio)phosphoric acid trianilide | Variable |

The above ingredients were mixed on a 2-roll laboratory rubber mill in conventional manner and the mixed sheeted stock was tested for scorch characteristics in a Mooney rotating disc Plastometer and cure characteristics in an oscillating disc Rheometer. The results are tabulated below:

| Retarder | Mooney Scorch at 130°C Minimum + 10 (Minutes) | Rheometer Cure Characteristics at 130°C | | |
| --- | --- | --- | --- | --- |
| | | Induction Time $T_2$ (Minutes) | Torque at 95% Peak (inch lbs.) | Time to reach 95% Peak Torque (Minutes) |
| Nil | 9 | 7.4 | 60 | 21.4 |
| 0.1 | 14.5 | 9.5 | 61.9 | 22.7 |
| 0.2 | 18.5 | 11.5 | 61.9 | 25.2 |
| 0.3 | 23 | 12.7 | 62.3 | 26.5 |
| 0.5 | 31 | 15.0 | 61.4 | 28.8 |

| Retarder | Mooney Scorch at 130°C Minimum + 10 (Minutes) | Rheometer Cure Characteristics at 130°C | | |
|---|---|---|---|---|
| | | Induction Time $T_2$ (Minutes) | Torque at 95% Peak (inch lbs.) | Time to reach 95% Peak Torque (Minutes) |

-continued

Example 3

| | |
|---|---|
| SBR | 100 |
| High Abrasion Furnace Black | 52 |
| High Aromatic Oil | 10 |
| Zinc Oxide | 3.5 |
| Stearic Acid | 1.5 |
| Sulphur | 1.8 |
| N-Cyclohexyl-2-benzthiazylsulphenamide | 1.2 |
| N,N$^1$,N$^{11}$-tris (isopropylthio) phosphoric acid trianilide | Variable |

The above ingredients were mixed and tested as in Example 2 The results are tabulated below:

TABLE II

| Retarder | Mooney Scorch at 130°C Minimum + 10 (Minutes) | Rheometer Cure Characteristics at 130°C | | |
|---|---|---|---|---|
| | | Induction Time $T_2$ (Minutes) | Torque at 95% Peak (inch lbs.) | Time to reach 95% Peak Torque (Minutes) |
| Nil | 34 | 10.3 | 57.2 | 21.8 |
| 0.1 | 41.5 | 11.8 | 55.3 | 23.4 |
| 0.2 | 48 | 13.3 | 55.4 | 24.2 |
| 0.3 | 58 | 14.4 | 52.5 | 25.1 |
| 0.5 | 62 | 15.0 | 53.9 | 25.5 |

EXAMPLE 4

Using the rubber mix described in Example 2 but substituting N-cyclohexyl-2-benzthiazyl sulphenamide by 2-mercaptobenzothiazole and testing in a similar manner, the following results were obtained:

TABLE III

| Retarder | Mooney Scorch at 120°C Minimum + 10 (Minutes) | Rheometer Cure Characteristics at 150°C | | |
|---|---|---|---|---|
| | | Induction Time $T_2$ (Minutes) | Torque at 95% Peak (inch lbs.) | Time to reach 95% Peak Torque (Minutes) |
| Nil | 9 | 4.6 | 52.7 | 21 |
| 0.1 | 12½ | 5.4 | 52.6 | 21 |
| 0.2 | 17 | 6.1 | 53.6 | 21.5 |
| 0.3 | 23 | 7.0 | 53.6 | 21.5 |

Example 5

| | |
|---|---|
| Natural Rubber   Pale Crepe | 100 |
| Zinc Oxide | 10 |
| Stearic Acid | 1 |
| Blanc Fixe | 75 |
| Titanium Dioxide | 10 |
| Sulphur | 2.5 |
| 2-Mercaptobenzothiazole | 0.5 |

Mixing and testing for scorch characteristics was done in conventional manner as in previous examples. The results were as follows:

| | |
|---|---|
| Moony Scorch times at 130°C without retarder | 7 Minutes |
| Moony Scorch times at 130°C with 0.25 parts of N,N$^1$,N$^{11}$-tris (isopropylthio) phosphoric trianilide | 16½ Minutes |

EXAMPLE 6

A solution of 22.1 parts of isopropyl sulphenyl chloride in 150 parts of cyclohexane is added to a suspension of 32.2 parts of N,N$^1$-diphenyl-p-tolyl phosphuric diamide and 20.2 parts of triethylamine in 150 parts of toluene. The reaction mixture is stirred for 1 hour. Insoluble material is filtered off, and the filtrates are concentrated under reduced pressure to leave a yellow oil which is chromatographed over silica gel. Elution with carbon tetrachloride gives 36 parts of N,N'-bis-(isopropylthio)-N,N'-diphenyl p-tolylphosphinic diamide as a colourless solid m.p. 87-88°C.
Found C, 63.1; H, 6.6; N, 4.6; P, 6.0; S, 13.4 percent;

$C_{25}H_{31}N_2OPS_2$ requires C, 63.8; H, 6.6; N, 5.95; P, 6.6; S, 13.6 percent.

EXAMPLE 7

A solution of 33.15 parts of isopropyl sulphenyl chloride in 150 parts of cyclohexane is added to a stirred suspension of 34.1 parts of N,N$^1$,N$^{11}$-tricyclohexylphosphoric triamide and 30.3 parts of triethylamine in 30 parts of cyclohexane. The reaction is exothermic but easily controlled and after the addition is complete the mixture is stirred for a further 1 hour. Insoluble material is filtered off and the filtrates evaporated under reduced pressure and the residue is chromatographed over silica gel. Elution with carbon tetrachloride yields 16 parts of N,N$^1$,N$^{11}$-tricyclohexyl-N,N$^1$N$^{11}$-tris(isopropylthio)phosphoric triamide as a pale yellow oil. Found C, 55.1; H, 9.3; N, 7.3; P, 5.6%, $C_{27}H_{54}N_3OPS_3$ requires C, 57.6%; H, 9.6%; N, 7.5%; P, 5.5%.

EXAMPLE 8

A solution of 44.2 parts of isopropyl sulphenyl chloride in 150 parts of cyclohexane is added to a solution of 35 parts of N,N$^1$,N$^{11}$-triisobutylphosphoric triamide and 40.4 parts of triethylamine in 150 parts of cyclohexane at room temperature. After stirring for 1 hour the insoluble triethylamine hydrochloride is filtered off. The filtrates are washed with 10% hydrochloric acid, 10% sodium bicarbonate and finally water. The organic layer is dried over anhydrous magnesium sulphate and evaporated at reduced pressure. The residue is chromatographed over silica gel. Elution with carbon tetrachloride gives 21 parts of N,N$^1$N$^{11}$-triisobutyl-N,N$^1$,N$^{11}$ tris(isopropylthio)phosphoric triamide as a yellow oil. Found N, 9.1; S, 18.2 percent; $C_{21}H_{48}N_3OPS_3$ requires N, 8.7; P, 19.8 percent. The structure is confirmed by N.M.R. spectoscopy.

EXAMPLE 9

A solution of 9.2 parts of 2-formyl-2-methylethyl sulphenyl chloride in 150 parts of carbon tetrachloride is added to a suspension of 22.9 parts of N,P,-triphenylphosphinic amide and 6.74 parts of triethylamine in 150 parts of carbon tetrachloride at room temperature. The reaction mixture is stirred for a further 1 hour. The insoluble material is filtered off and the filtrate evaporated under reduced pressure to give a viscous liquid which is chromatographed over silica gel. Elution with chloroform yields 2 parts of N,N,P-triphenyl-N-(2-formyl-2-methylethylthio)phosphinic amide as a colourless solid, m.p. 168°–171°C. The infra red and nuclear magnetic resonance spectra are consistant with the indicated structure.

EXAMPLE 10

A solution of 11.1 parts of isopropyl sulphenyl chloride in 100 parts of carbon tetrachloride is added to a suspension of 30.9 parts of N,P,P-triphenylphosphinic amide and 10.0 parts of triethylamine in 150 parts of carbon tetrachloride at room temperature. The mixture is stirred for a further 1 hour. The triethylamine hydrochloride is filtered off and the filtrates evaporated under reduced pressure to give a white solid. This is recrystallised from methylated spirits to yield 16.5 parts of N-isopropylthio-N,P,P-triphenylphosphinic amide as a colourless solid m.p. 148°–150°C. Found, C, 67.2; H. 6.2; N, 4.0; P, 8.1 percent, $C_{21}H_{22}NOPS$ requires C, 68.7; H, 6.0; N, 3.8; P, 8.45 percent. The NMR spectrum is consistent with the proposed structure.

EXAMPLE 11

A solution of 43.35 parts of phenyl sulphenyl chloride in 100 parts of cyclohexane is added to a suspension of 32.3 parts of phosphoric trianilide and 30.7 parts triethylamine in 100 parts of cyclohexane at room temperature. The reaction mixture is stirred a further one hour, and filtered. The filtrates are washed with water, dried and solvent removed under reduced pressure leaving a yellow oil. On trituration with petroleum ether b.p. 40°–60° a white solid is obtained. Crystallisation from aqueous cellusolve gave 11.4 parts of N,N$^1$,N$^{11}$-tris(phenylthio)-N,N$^1$,N$^{11}$-triphenyl phosphoric triamide as a colourless solid m.p. 145°–147°C. Micro analysis, NMR and IR and constant with the indicated structure.

EXAMPLE 12

A solution of 37.35 parts of n-butyl sulphenyl chloride in 100 parts of carbon tetrachloride is added to a stirred suspension of 32.3 parts of phosphoric trianilide and 30.3 parts of triethylamine in 100 parts of carbon tetrachloride at room temperature. The reaction mixture is stirred for a further 1 hour, and filtered. The filtrates are evaporated under reduced pressure and the residue is chromatographed over silica gel to give 19 parts of N,N$^1$,N$^{11}$-tris(n-butyl)-N,N$^1$N$^{11}$-triphenyl phosphoric triamide as a pale yellow oil. The I.R., N.M.R. and micro analysis is consistent with the indicated structure.

EXAMPLE 13

A solution of 22.6 parts of cyclohexane sulphenyl chloride in 100 parts of cyclohexane is added to a stirred suspension of 16.7 parts of N,N$^1$,N$^{11}$-triphenyl phosphoric triamide and 18.0 parts of triethylamine in 200 parts of cyclohexane. When the addition is complete the mixture is heated to reflux for 30 minutes, filtered hot and the filtrate evaporated down under reduced pressure. The residue is crystallised from diethyl ether to give 12.5 parts of N,N$^1$,N$^{11}$-tris (cyclohexylthio)-phosphoric trianilide as a colourless solid, m.p. 137°–138°.

EXAMPLE 14

A solution of 16.55 parts of isopropyl sulphenyl chloride in cyclohexane is added to a stirred suspension of 18.27 parts of N,N$^1$,N$^{11}$-tris(4-methoxyphenyl)phosphoric triamide and 18.0 parts of triethylamine in 100 parts of cyclohexane. After filtering off insoluble material the filtrate is evaporated to small volume under reduced pressure whereupon 10.8 parts of N,N$^1$,N$^{11}$-tris(isopropylthio) N,N$^1$,N$^{11}$-tris(4-methoxyphenyl)-phosphoric triamide are obtained as a colourless solid, m.p. 106°–108°.

EXAMPLE 15

A solution of 11.05 parts of isopropyl sulphenyl chloride in 100 parts of cyclohexane is added to a stirred mixture of 16.2 parts of phenyl N,N$^1$-diphenylphosphorodiamidate and 16 parts of triethylamine in 100 parts of cyclohexane. The mixture is heated to 70° for 1 hour, insoluble material filtered off and the filtrate evaporated to small volume whereupon phenyl N,N$^1$-diphenyl-N,N$^1$-bis(isopropylthio)phosphorodiamide (5.0 parts) crystallises as a colourless solid, m.p. 56°–57°.

EXAMPLE 16

A solution of 20.05 parts of 4-tert.-butyl phenylsulphenyl chloride in 100 parts of carbon tetrachloride is added dropwise to a stirred mixture of 10.7 parts of phosphoric trianilide, 10.1 parts of triethylamine and 0.5 parts of dimethylformamide in 100 parts of toluene. The mixture is stirred at 40° for 30 minutes, filtered and the filtrate is evaporated down under reduced pressure to leave a pale yellow oil which, on chromatography over silicagel gives N,N$^1$,N$^{11}$-triphenyl N,N$^1$,N$^{11}$-tris(4-tert.-butylphenylthio) phosphoric triamide (4.3 parts) as a colourless solid, m.p. 174°–175°.

EXAMPLE 17

Using the basic rubber compostions and procedure given in Example 2, further additives were tested for scorch characteristics in a "Mooney" rotating disc plastometer. The results are given in Table IV below.

TABLE IV

| Retarder | Parts by Weight | Temp. °C | Mooney "Scorch" Time for Minimum + 10 Units (Minutes) |
|---|---|---|---|
| Nil | — | 130° | 10 |
| Product described in Example 6 | 0.25 | 130° | 22 |
| Product described in Example 10 | 0.25 | 130° | 19 |
| Product described in Example 13 | 0.25 | 130° | 21 |
| Product described in Example 14 | 0.25 | 130° | 20 |
| Nil | — | 120° | 23 |
| Product described in Example 7 | 0.3 | 120° | 25 |
| Product described in Example 8 | 0.3 | 120° | 25 |
| Product described in Example 9 | 0.25 | 120° | 33 |
| Product described in Example 11 | 0.25 | 120° | 41 |
| Product described in Example 12 | 0.25 | 120° | 36 |
| Product described in Example 15 | 0.25 | 120° | 48 |

EXAMPLE 18

The rubber composition given in Example 2 was mixed in the manner described. Test sheets were vulcanised in a stream heated laboratory press by heating for 15 minutes at 153°C. Appropriate test pieces were cut from the vulcanisates and their physical properties determined by the procedures of current British Standard Specification BS-903. The results were as follows:

TABLE V

| Physical Property | Without Retarder | With 0.25 Parts of Retarder | With 0.5 Parts of Retarder |
|---|---|---|---|
| Hardness | 64.5° | 64° | 63.5° |
| Resilience (%) at 18°C | 66.7 | 67 | 65.8 |
| Tensile Strength (MN/M$^2$) | 29.4 | 30.2 | 29.2 |
| Elongation at Break (%) | 430 | 430 | 420 |
| Modulus at 300% (MN/M$^2$) | 19.7 | 20.2 | 19.2 |
| Tensile strength after ageing in cell-oven at | | | |
| 100°C for 2 days (MN/M$^2$) | 17.4 | 18.1 | 19.0 |
| 100°C for 4 days (MN/M$^2$) | 7.9 | 9.2 | 9.2 |
| 100°C for 6 days (MN/M$^2$) | 5.7 | 5.9 | 4.9 |

EXAMPLE 19

The rubber composition given in Example 3 was mixed in the manner described. Test sheets were vulcanised in a steam heated laboratory press by heating for 30 minutes at 153°C. Appropriate test pieces were cut from the vulcanisates and their physical properties determined by the procedures of current British Standard Specification B.S.-903. The results were as follows:

TABLE VI

| Physical Property | Without Retarder | With 0.25 Parts of Retarder | With 0.5 Parts of Retarder |
|---|---|---|---|
| Hardness (B.S.°) | 62.5 | 62.5 | 63 |
| Resilience (%) | 48.3 | 48.3 | 47.2 |
| Tensile Strength (MN/M$^2$) | 24.0 | 25.1 | 24.8 |
| Elongation at Break (%) | 480 | 495 | 470 |
| Modulus at 100% (MN/M$^2$) | 3.5 | 3.7 | 4.3 |
| After ageing 2 days at 100°C in cell-overn: | | | |
| Tensile Strength (MN/M$^2$) | 23.8 | 23.9 | 23.0 |
| Modulus at 100% (MN/M$^2$) | 5.2 | 7.2 | 8.4 |
| Elongation at Break (%) | 370 | 330 | 300 |
| After ageing for 4 days at 100°C in cell-oven: | | | |
| Tensile strength (MN/M$^2$) | 22.4 | 22.2 | 21.8 |
| Modulus at 100% (MN/M$^2$) | 8.4 | 8.1 | 9.1 |
| Elongation at Break (%) | 280 | 270 | 260 |
| After ageing for 6 days at 100°C in cell-oven: | | | |
| Tensile strength (MN/M$^2$) | 21.4 | 21.8 | 22.0 |
| Modulus at 100% (MN/M$^2$) | 9.4 | 9.0 | 10.0 |
| Elongation at Break (%) | 260 | 265 | 265 |

| Example 20 | Parts |
|---|---|
| Natural Rubber Smoked Sheets | 100 |
| Zinc Oxide | 3.5 |
| Stearic Acid | 3 |
| High-abrasion Furnace Black | 45 |
| Process Oil | 3.5 |
| Sulphur | 2.5 |
| Dibenzthiazyldisulphide | 0.5 |
| N,N$^1$,N$^{11}$-Tris(trichloromethylthio)phosphoric acid trianilide | 0 or 0.5 |

The above tread type composition was mixed on a laboratory mill and tested as described in Example 2. The results were as following:

TEST VII

| Test | Without Retarder | With 0.5 p.h.r. Retarder |
| --- | --- | --- |
| Mooney Scorch at 120°C (Minimum + 10) minutes | 14.75 | 17.75 |
| Rheometer at 150°C | | |
| Induction Time ($T_2$) Mins. | 5.7 | 6.5 |
| Peak Torque (inch lbs.) | 50.1 | 50.6 |
| Time to 90% Peak (Mins.) | 20.7 | 23.3 |

The $N,N^1,N^{11}$-tris(trichloromethylthio)phosphoric acid trianilide used above is a cream-coloured solid, meeting at 64°–65°C, and was prepared by the procedure described in Example 1 using trichloromethylsulphenyl chloride in place of isopropylsulphenyl chloride.

| Example 21 | Parts |
| --- | --- |
| Natural Rubber Smoked Sheets | 100 |
| Zinc Oxide | 3.5 |
| Stearic Acid | 1.5 |
| General Purpose Furnace Black | 35 |
| Process Oil | 3 |
| Sulphur | 2.5 |
| Dibenzthiazyldisulphide | 1.0 |
| Retarder as in Example 20 | 0 or 0.5 |

The above tyre-casing type composition was mixed and tested as in Example 20. The results were as following:

TABLE VIII

| Test | Without Retarder | With 0.5 p.h.r. Retarder |
| --- | --- | --- |
| Mooney Scorch at 120°C (Minimum + 10) Minutes | 16 | 19.25 |
| Rheometer at 150°C | | |
| Induction time ($T_2$) Mins. | 6.1 | 6.8 |
| Peak Torque (in. lbs.) | 48.4 | 52.4 |
| Time to 90% Peak (Mins.) | 16.8 | 24.1 |

We claim:
1. An amide of the formula

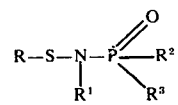

wherein R is alkyl of up to 18 carbon atoms, 2-formylprop-2-yl, alkenyl of up to 18 carbon atoms, cyclopentyl, cyclohexyl, phenyl, tolyl, butyl phenyl, naphthyl, β-methyoxyethyl, β-cyanoethyl, 4-chlorophenyl, 4-methoxyphenyl, 4-dimethylaminophenyl, 2-nitrophenyl, 4-nitrophenyl, 2,3,4,5,6-pentachlorophenyl, 2-methoxycarbonylphenyl or 4-phenylsulphonylphenyl; $R^1$ is hydrogen, alkyl of up to 18 carbon atoms, 2-formylprop2-yl, alkenyl of up to 18 carbon atoms, cyclopentyl, cyclohexyl, phenyl, tolyl, naphthyl, β-methoxyethyl, β-cyanoethyl, 4-chlorophenyl, 4-methoxyphenyl, 4-dimethylaminophenyl, 2-nitrophenyl, 4-nitrophenyl, 2,3,4,5,6-pentachlorophenyl, 2-methoxycarbonylphenyl, 4-phenylsulphonylphenyl, p-toluene sulphonyl, acetyl or N=CH-R where R has the meaning stated above; $R^2$ and $R^3$ are each a group $R-S-NR^1$ where each of R and $R^1$ have the meaning stated above, hydrogen, halogen, a value as recited for R, 2-benzothiazolylthio, 2-benzoxazolythio, 2-benzimidazolylthio, 2-pyrimidinylthio or 2-triazinylthio groups, amino, ethylamino, diethylamino, dimethylamino, phenylamino, methylphenylamino or ethylphenylamino; or $R^2$ and $R^3$ together with the phosphorus atom joining them form 2-oxo-1,3,2-diazaphospholane, 2-oxo-4,5-benzo-1,3,2-diazaphospholane, 2-oxo-1,3,2-oxazaphospholane, 2-oxo-4,5-benzo-1,3,2-oxazaphospholane, 2-oxo-4,5-benzo-1,3-thiazaphospholane, or 2-oxo-2,3-dithiaphospholane.

2. An amide as claimed in claim 1 wherein R is a secondary alkyl, cyclopentyl or cyclohexyl.

3. An amide as claimed in claim 1 wherein $R^1$ is phenyl.

4. An amide as claimed in claim 1 wherein one or both of $R^2$ and $R^3$ is a group $R-S-NR^1$.

* * * * *